United States Patent
Sugita (10) Patent No.: US 7,799,277 B2
(45) Date of Patent: Sep. 21, 2010

(54) DETECTION DEVICE AND DETECTION METHOD

(75) Inventor: Mitsuro Sugita, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 796 days.

(21) Appl. No.: 10/543,919

(22) PCT Filed: Dec. 6, 2004

(86) PCT No.: PCT/JP2004/018527

§ 371 (c)(1), (2), (4) Date: Jul. 29, 2005

(87) PCT Pub. No.: WO2005/054328

PCT Pub. Date: Jun. 16, 2005

(65) Prior Publication Data

US 2006/0147350 A1    Jul. 6, 2006

(30) Foreign Application Priority Data

Dec. 8, 2003   (JP)   .............. 2003-408933

(51) Int. Cl.
*B01L 3/00* (2006.01)
(52) U.S. Cl. ............. 422/100; 422/99; 422/50
(58) Field of Classification Search ......... 422/100, 422/211; 435/7.1; 436/180
See application file for complete search history.

(56) References Cited

U.S. PATENT DOCUMENTS

| | | | | |
|---|---|---|---|---|
| 5,064,263 A * | 11/1991 | Stein | ............ | 385/14 |
| 6,007,775 A | 12/1999 | Yager | | |
| 6,036,927 A * | 3/2000 | Chatterjee et al. | ........... | 422/211 |
| 6,541,213 B1 * | 4/2003 | Weigl et al. | ........... | 435/7.1 |
| 2003/0017079 A1 * | 1/2003 | Hahn et al. | ........... | 422/82.09 |
| 2003/0036206 A1 * | 2/2003 | Chien et al. | ........... | 436/180 |
| 2003/0211507 A1 | 11/2003 | Hatch et al. | | |
| 2006/0123900 A1 | 6/2006 | Sugita | ........... | 73/204.26 |

FOREIGN PATENT DOCUMENTS

| | | |
|---|---|---|
| JP | 3-053136 | 3/1991 |
| JP | 3-295448 | 12/1991 |
| JP | 04-032747 | * 2/1992 |

(Continued)

OTHER PUBLICATIONS

Migiwa, Ando, Concentration Measuring Instrument, Feb. 4, 1992, Patent Abstracts of Japan, pp. 1-2.*

(Continued)

*Primary Examiner*—Walter D Griffin
*Assistant Examiner*—Christine T Mui
(74) *Attorney, Agent, or Firm*—Fitzpatrick, Cella, Harper & Scinto (57) ABSTRACT

A detection device is provided which comprises an examination flow channel for passing a fluid containing a detection object, a reference flow channel extending adjacently along the examination flow channel, an interaction film interposed between the examination flow channel and the reference flow channel for causing an interaction thereof, a light emission unit for injecting a detecting light into the reference flow channel, and a detection unit for receiving the detecting light. This device is used for recognizing the state of the detection object in the examination flow channel from deflection of the optical path of the detecting light caused by the interaction.

11 Claims, 10 Drawing Sheets

FOREIGN PATENT DOCUMENTS

| | | |
|---|---|---|
| JP | 6-167469 | 6/1994 |
| JP | 2691374 | 9/1997 |
| JP | 2747933 | 2/1998 |
| WO | WO 99/05512 | 2/1999 |
| WO | WO 02/40874 * | 5/2002 |

OTHER PUBLICATIONS

Waters, et al., "Microchip Device for Cell Lysis, Multiplex PCR Amplification, and Electrophoretic Sizing," Analytical Chemistry, vol. 70, No. 1, Jan. 1, 1998, pp. 158-162.

* cited by examiner

DETECTION DEVICE AND DETECTION METHOD

TECHNICAL FIELD

The present invention relates to a detection device and a detection method employing a micro total analysis system (μ-TAS) for detecting a fine distribution of pressure or temperature, for determining a concentration of a substance, or for obtaining biological information or genetic information contained in a fluid, or the like of a fluid flowing through a flow channel in a system.

BACKGROUND ART

Various types of detection devices have been developed for obtaining various data of a fluid by passing an objective fluid through a detection flow channel in the device. The detection devices include electrical detection devices for measuring the concentration or temperature of an objective substance in a fluid, and optical detection devices for measuring the concentration of an objective substance in a fluid. Known optical detection devices include concentration detection devices which introduce detecting light from a light source into a fluid, measure a quantity of transmitted light, and calculate the concentration; and devices which measure the concentration and temperature of an objective substance from light concentration or light divergence by a lens effect. In such devices, generally, a laser beam of about 1 mm diameter is allowed to penetrate through a flowing liquid in a flow channel of about 10 cm long and about 5 mm wide, and refractive index distribution in the sectional radial direction of the circular tube is derived by detecting the focusing point to measure the concentration of an objective substance in the fluid. For detection of the focusing point of the light beam or the maximum light intensity position, the beam diameter or the light intensity is measured by a photodiode (PD) or a measuring instrument called generally a beam analyzer.

Japanese Patent 2747933 discloses a concentration measurement method conducted as shown below. A catalyst immobilized on an outer wall of a tubular member catalyzes a reaction of a substrate substance to be detected in a fluid to cause heat generation or heat absorption. Consequently, the medium within the tubular member is heated or cooled by the wall of the tubular member to cause expansion or constriction and to cause a nonuniform density distribution from the center toward the outer wall in the tube, resulting in a nonuniform refractive index distribution. Upon introduction of detecting light into the medium, the light beam is deflected owing to the nonuniform refractive index distribution and is focused at a certain position. The refractive index distribution is determined from the focus position of the detecting light to show the heated or cooled state of the medium. This heated or cooled state shows the degree of the reaction of the substrate on the outer wall. From this, the concentration of the substrate is determined.

Japanese Patent 2691374 discloses a concentration measurement method conducted as below. An objective substrate in a fluid having been introduced into an outer frame is allowed to penetrate a porous wall of a tube constituted of a porous material to dissolve and diffuse into the medium in the tube. Thereby, the substrate concentration changes gradually toward the axis of the tube. Upon introduction of detecting light from one end of the tube, the light is converged toward the center of the tube, or is diverged outward from the center. By receiving this detecting light, change of the beam diameter, energy density, or converged point is measured, and therefrom the refractive index distribution is measured. From the refractive index distribution, the substrate concentration distribution in the medium is derived, and further the concentration of the substrate in the detection-objective fluid in the outer frame is estimated.

In recent years, micro total analysis systems (μ-TAS) have been developed which conduct detection or measurement in a small scale to decrease the quantity of an examination sample, to reduce the cost, or to simplify the operation. This μ-TAS is a system which utilizes fine flow channel formed on a chip in a size of from several millimeters to several centimeters by a technique of MEMS (microelectro-mechanical system) or the like and conducts various examination of measurement in the flow channel.

However, it is difficult to utilize the μ-TAS in the optical detection method employing conventional device constituted usually of a flow channel of about 10 cm long and 5 mm wide because of liability to insufficiency of measurement accuracy and response speed. In other words, the complicated constitution employed in the conventional detection device hinders realization of high integration, the feature of the μ-TAS.

Electrical measurement by the μ-TAS, for example, is liable to be affected by an electric noise, resulting in a low measurement accuracy. Absorption measurement by the μ-TAS, at a high concentration of the detection-objective substance in the examined fluid, is conducted optically with very small quantity of the light for the signal generation owing to light absorption to give a low S/N ratio (signal to noise ratio). On the other hand, with an examination-objective fluid diluted to avoid the drop of the S/N ratio, the signal itself becomes weak to retard difficult the measurement with a high S/N ratio. Measurement by optical focus detection employs necessarily a beam analyzer in a large size of tens of centimeters, which is not suitable for the μ-TAS. Detection with a simple PD conducts detection of light intensity at plural positions by moving the PD along the beam, which makes complicated the constitution to hinder miniaturization and high degree of integration even with the μ-TAS.

In the inventions of Japanese Patents 2747993 and 2691374, the tube constituted of alumina or the like employed necessarily for the invention should be precise in the shape and dimension not to affect adversely the light refractivity and converging position. Such a tube cannot readily be prepared, and will be of a high production cost, and may makes troublesome the handling and operation.

DISCLOSURE OF THE INVENTION

The present invention intends to provide a detection device which is useful for high-precision measurement of various data regarding a fluid and is miniaturized and highly integrated, and which can be produced readily with high precision. The present invention intends also to provide a detection method employing a μ-TAS with the aforementioned detection device.

According to an aspect of the present invention, there is provided a detection device, comprising:
an examination flow channel for passing a fluid containing a detection object,
a reference flow channel extending adjacently along the examination flow channel,
an interaction film located between the examination flow channel and the reference flow channel and capable of causing an interaction therefrom,
a light emission unit for irradiating the reference flow channel with a detecting light, and
a detection unit for receiving the detecting light; and recognizing the state of the detection object in the examination flow channel from a deflection of the optical path of the detecting light caused by the interaction.

The interaction film is preferably a semipermeable membrane, and the interaction is preferably a penetration of the fluid from the examination flow channel into the reference flow channel, and the detection unit preferably measures the concentration of the detection object in the examination flow channel. The detection unit preferably comprises plural optical detectors arranged in the substantially same direction of arrangement as of the examination flow channel and the reference flow channel, and the deflection of the optical path of the detecting light is evaluated by differential output of the plural optical detectors.

The interaction film is preferably a heat-conductive film; the interaction is heat transfer from the examination flow channel to the reference flow channel; and the detection unit preferably measures temperature change in the examination flow channel. The examination flow channel preferably has plural fluid inlets for introduction of different substances.

According to another aspect of the present invention, there is provided a detection method comprising the steps of:

providing a detection device which is comprised of an examination flow channel, a reference flow channel extending adjacently along the examination flow channel, and an interaction film located between the examination flow channel and the reference flow channel for causing an interaction therebetween, introducing a fluid examination object into the examination flow channel, irradiating the reference flow channel with a detecting light in which an interaction with the examination flow channel has been caused through the interaction film, measuring a deflection of the optical path of the detecting light caused by the interaction, and recognizing the state of the examination object in the examination flow channel from the deflection.

According to the present invention, the state of an examination object in an examinationexamination flow channel can be detected by causing an interaction between an examinationexamination flow channel and a reference flow channel through an interaction film, and detecting deflection of an examination light introduced to the reference flow channel to determine the interaction degree. The device of the present invention does not require movement of the detection unit, and does not employ a tube which is complicated in production, so that the constitution is simple and the production cost of the device is low.

BEST MODE FOR CARRYING OUT THE INVENTION

The interaction film may be a semipermeable membrane: The interaction may be penetration of the fluid from an examination flow channel into a reference flow channel; and the detection unit may be the one which measures the concentration of the fluid in the examination flow channel. Otherwise, the interaction film may be a heat-conducting film; the interaction may be heat transfer from the examination flow channel to the reference flow channel; and the detection unit may be the one which measures temperature change in the examination flow channel. When the heat is a reaction heat of a chemical reaction, the state of the chemical reaction can be examined by the temperature change measurement.

The examination flow channel may be provided with plural inlets for introducing different substances into the examination flow channel. In such an embodiment, a chemical reaction may be caused between the introduced substances, and the state of the chemical reaction can be examined by measurement of the reaction heat.

The detection unit may have plural photodetectors arranged substantially in the direction of arrangement of the examination flow channel and the reference flow channel. The deflection of the optical path of the detecting light can be observed by the differential output from the plural photodetectors.

The detection device of the present invention can be constituted from a plate-shaped functional module having an examination flow channel and a reference flow channel having a width ranging from 10 μm to 100 μm with a μ-TAS or the like by employing a MEMS technique. Thereby, the device can be produced readily and can be miniaturized with high precision.

The detection device and detection method of the present invention employing a μ-TAS enables the following matters:

utilization of a gradient index prism (GRIN prism);

high-precision measurement of the properties such as the concentration of a detection-objective substance flowing in the examination flow channel independently of the concentration of the detection-objective substance;

facilitation of measurement and treatment with the same system even with high-integrated plural flow channels;

direct transmission of signals corresponding to the information in the examination flow channel at a velocity of light, the physical limit; and direct treatment of parallel output by transmitting the information in parallel with a simple constitution by output from an array constitution having plural flow channels.

Embodiments of the present invention are explained below more specifically.

FIRST EMBODIMENT

A first embodiment of the present invention is a concentration detection device of a GRIN prism system employing asymmetric flow channels. Firstly, the basic constitution is explained of the concentration detection device of this embodiment.

Figure 1:
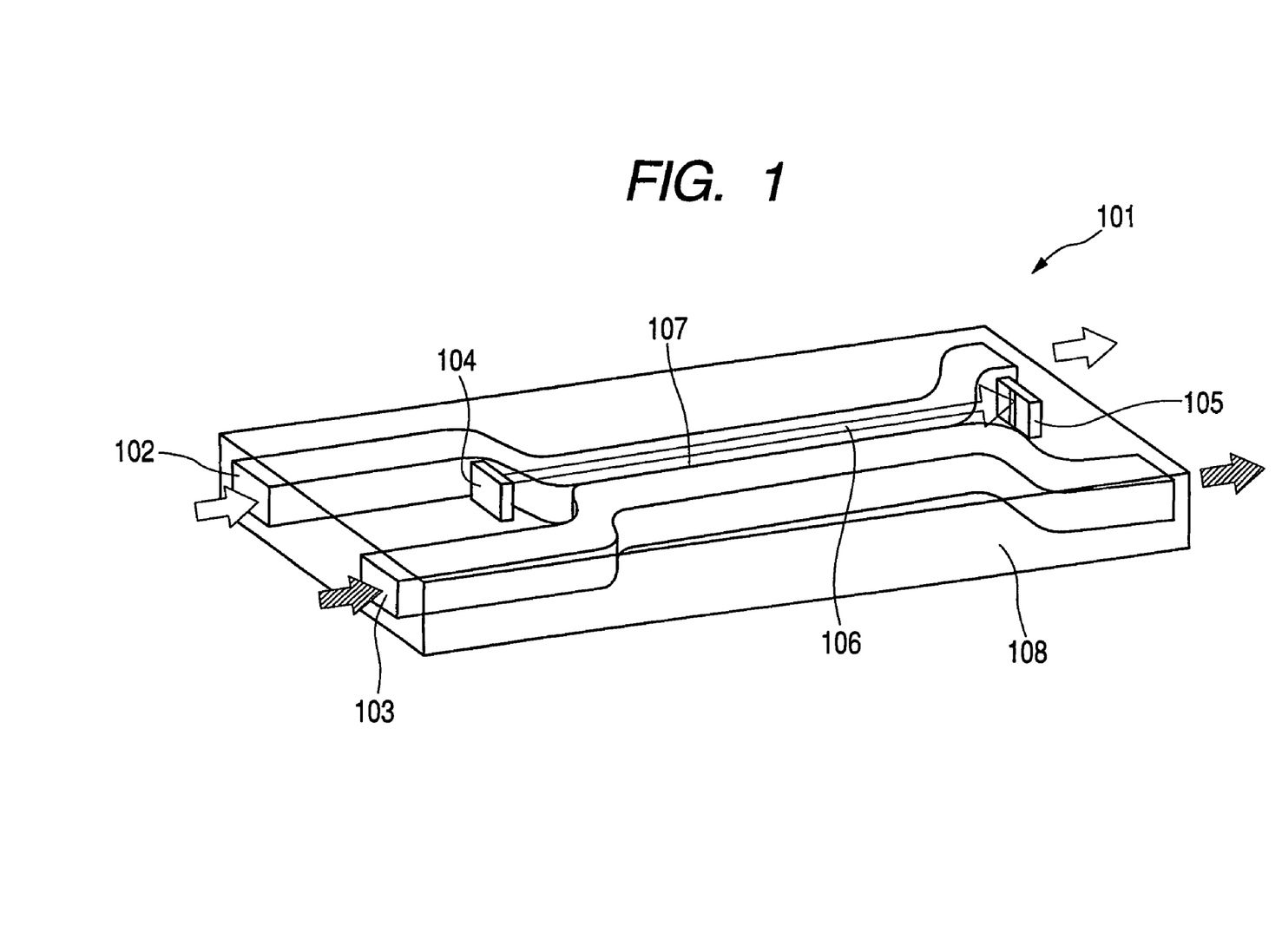
FIG. 1 is a perspective view of constitution of the detection device of First Embodiment of the present invention.

FIG. 1 is a perspective view illustrating schematically the concentration detection device of this embodiment consisting of a plate-shaped functional module 101. This functional module 101 is used for determination of a concentration of an examination-objective substance in a fluid to be examined. Functional module 101 has reference flow channel 102, and examination flow channel 103 for flow of the examination-objective fluid. The widths of the flow channels range from 10 μm to 100 μm. Reference flow channel 102 and examination flow channel 103 are partitioned with semipermeable membrane 107. Therefore, the semipermeable membrane constitutes the wall between the adjacent flow channels, whereby a substance can permeate through semipermeable membrane 107 from examination flow channel 103 to reference flow channel 102 by the concentration difference between the flow channels. Semipermeable membrane 107 is formed, for example, from a porous material, which can be made suitably from various materials such as alumina, silicon, polymers, glass, and ceramics. The pore size and porosity of the porous material are suitably selected for the kind of the permeating examination object.

Most portions of the walls of reference flow channel 102 and examination flow channel 103 excluding the semipermeable membrane wall are constituted of the material of main body 108 of functional module 101 such as a silicon type material and a glass material, forming strong non-permeable walls. This module is different from the one having plural semipermeable membranes 107 symmetrically to the center axis line of the reference flow channel 102.

This functional module 101 has an optical path for detection: Light-emission unit 104 and detection unit 105 are placed in opposition at the ends of the semipermeable membrane portion of reference flow channel 102. Thereby, detecting light 106 from light-emission unit 104 passes through reference flow channel 102 to detection unit 105. The detection unit 105 has a so-called two-division sensor constituted of two light-intensity detectors which are placed in the arrangement direction of reference flow channel 102 and examination flow channel 103.

The principle of concentration detection of this embodiment is explained below.

An examination-objective fluid containing a detection-objective substance is allowed to flow through examination flow channel 103 of functional module 101, while a fluid containing no or a lower concentration of the detection-objective substance (hereinafter referred to as a "reference fluid") is allowed to flow through reference flow channel 102. The reference fluid may be a liquid derived by diluting the examination-objective fluid with water or the like. Thereby, the detection-objective substance will penetrate semipermeable membrane 107 into reference flow channel 102. The concentration of the detection-objective substance having penetrated is not uniform in the reference fluid, being higher near semipermeable membrane 107 and decreasing with the distance from semipermeable membrane 107.

Detecting light 106 is allowed to pass through the reference fluid in which the detection-objective substance is distributed nonuniformly. The detecting light 106 dose not travel straight in this fluid in which the refractive index of the reference fluid is nonuniformly distributed in proportion to the nonuniform concentration distribution in the reference fluid. The detecting light beam is curved in correspondence with the refractive index distribution according to the phenomenon called a GRIN (gradient index) lens effect or a GRIN prism effect. Specifically, the detecting light beam is curved toward the higher concentration portion in the solution. Consequently, the right-side and left-side light-intensity detectors of a two-division sensor as detection unit 105 detect respectively different light quantities and output corresponding different signals. The deflection of the light beam can be detected by the light quantity balance shown by the output difference. From the detected deflection, the concentration distribution of the detection-objective substance can be obtained, and the quantity of the detection-objective substance having penetrated through semipermeable membrane 107 into reference flow channel 102 can be estimated. Accordingly, the concentration of the detection-objective substance in the examination-objective fluid in examination flow channel 103 can be determined from the properties of semipermeable membrane 107, the concentration of the detection-objective substance in the reference fluid in reference flow channel 102, and the quantity of the detection-objective substance having permeated into reference flow channel 102.

In the examination-objective fluid flowing through examination flow channel 103, the detection-objective substance is contained substantially uniformly. Therefore, the light beam is little deflected in examination flow channel 103, not enabling the concentration measurement.

Figure 2A:
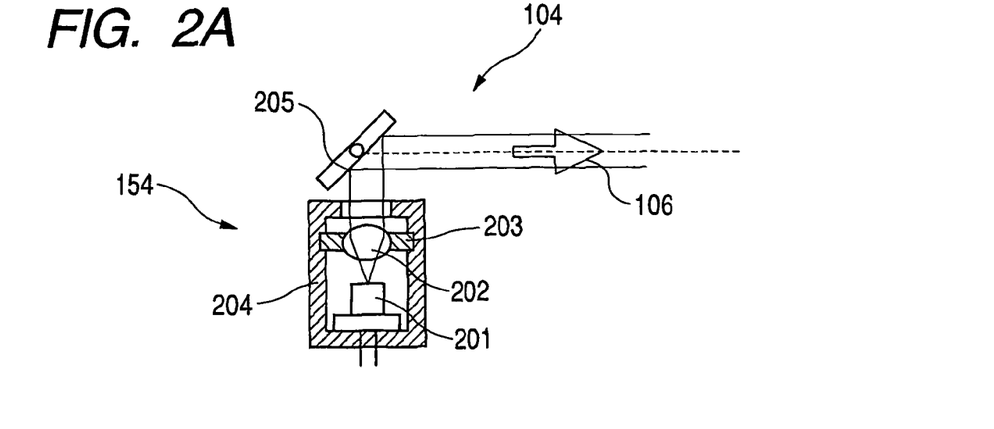
FIGS. 2A, 2B, and 2C are respectively a sectional view of a light-emission unit of the detection device of FIG. 1; a sectional view illustrating the optical path adjustment state thereof; and a block diagram illustrating in more detail the optical path-adjusting assembly.
Figure 2B:
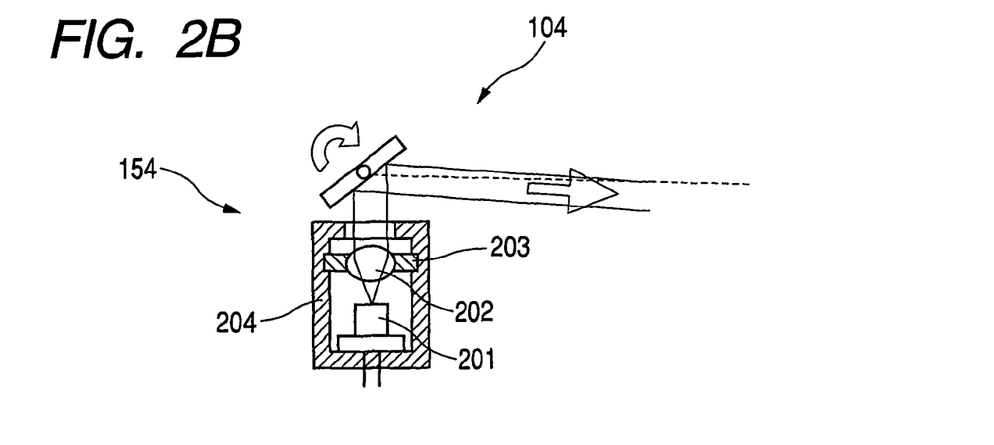
Figure 2C:
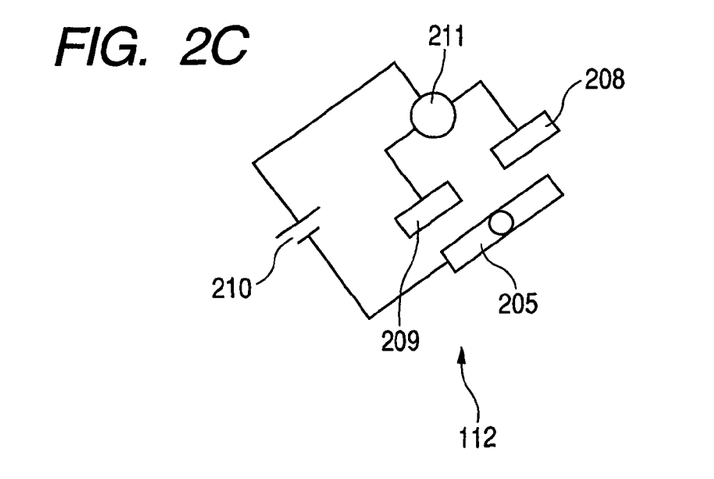

In this embodiment, the sensitivity of measurement of the light quantity balance can be raised by adjusting the position of the optical path on the light-receiving face of the detection unit in the initial state. FIGS. 2A, 2B, and 2C show the constitution for adjusting the optical path in the initial state.

As shown in FIGS. 2A and 2B, light-emission unit 104 of this Embodiment comprises a light emission unit main body and an optical path-adjusting assembly: the light-emission unit main body 154 has semiconductor laser 201 and collimater lens 202 held by cell 203, both encased in holder casing 204; and the optical path-adjusting assembly has turnable micromirror 205 counterposed to aperture of holder casing 204 and a mirror-turning mechanism. The directions of the light projection from semiconductor laser 201 and collimater lens 202 can be changed by turning micromirror 205 to irradiate the prescribed position. Specifically, in the initial state, detecting light 106 from light emission unit 104 is adjusted to direct to the center of the two-division sensor and to make the differential output from the two light-intensity detectors to be zero. FIG. 2C illustrates schematically the voltage source and the optical path-adjusting assembly. One end of voltage source 210 is connected to micromirror 205, and the other end is connected through changeover switch 211 to right electrode 208 and left electrode 209. Micromirror 205 is turnable by attraction by electrostatic force of the right or left electrode selected by changeover switch 211. Micromirror 205 is equipped with a restoration mechanism not shown in the drawing, whereby the turning angle of micromirror 205 can be adjusted finely and continuously by changing the voltage of the voltage source 210. Without the restoration structure, the turning angle can be adjusted by the constitution in which changeover switch 211 allots the voltage suitably to right and left electrodes 208, 209.

Otherwise, the position of detection unit 105 may be changed for adjusting the optical path in the initial state.

Figure 3A:
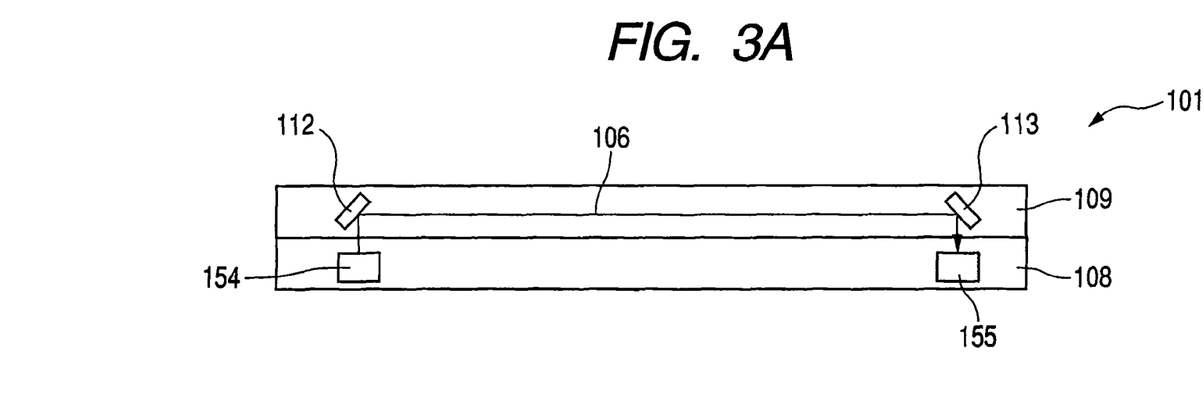
FIGS. 3A and 3B are respectively a schematic front view of the main portion of a modification of the detection device of FIG. 1, and a schematic plan view of another modification thereof.

In the constitution in which the optical path is adjustable by movable micromirror 205, the detection unit may be constructed in the same manner as the light-emission unit. That is, the detection unit may comprise the detection unit main body and an optical path-adjusting assembly having a micromirror. In this constitution, as shown in FIG. 3A, the functional module 101 may have a two-layer structure comprising a first layer 108 comprising flow channels 102, 103, light-emission unit main body 154, and detection unit main body 155; and a second layer 109 comprising optical path-adjusting assemblies 112, 113. Otherwise, in place of optical path-adjusting assemblies 112, 113, flow channel walls of flow channel 102, 103 may be constituted to function as the optical path-adjusting assembly.

Figure 3B:
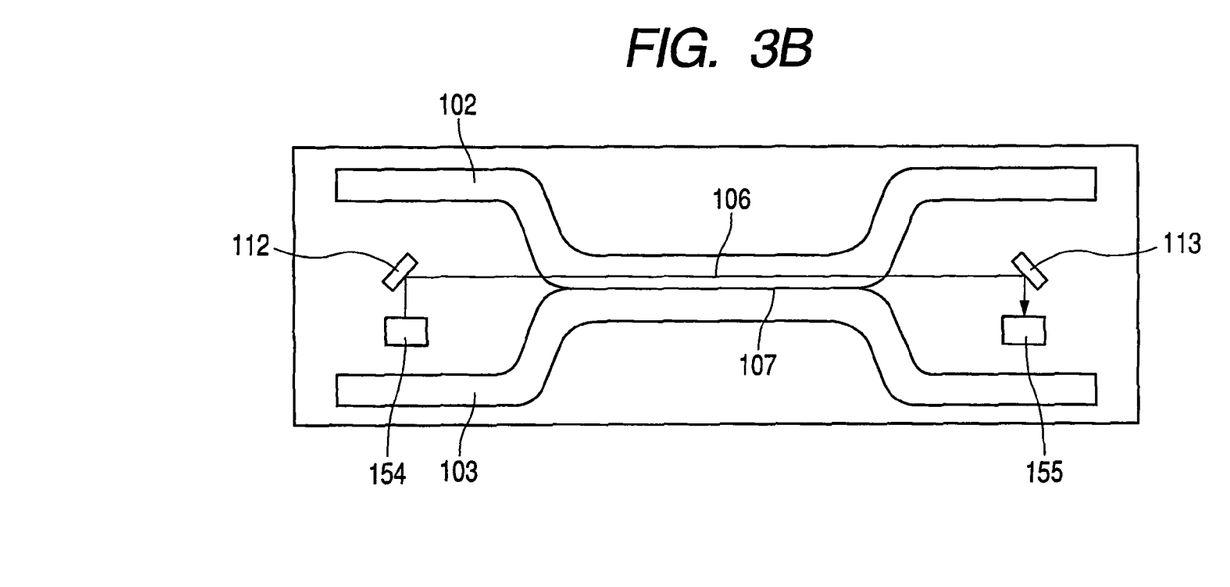

In the above constitution, as shown in FIG. 3B, light-emission unit main body 154, detection unit main body 155, optical path-adjusting assemblies 112, 113 together with flow channels 102, 103 may be all placed on the same plane; and optical path-adjusting assemblies 112, 113 may be constituted to deflect detecting light 106 within this plane.

Figure 4A:
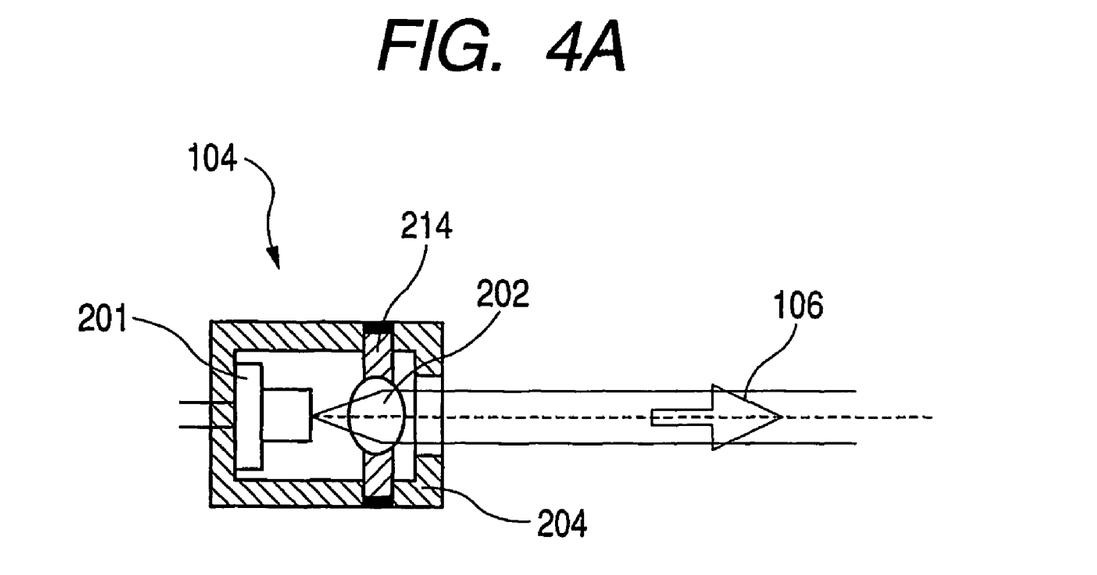
FIGS. 4A and 4B are respectively a sectional view of a modification of the light-emission unit; and a sectional view illustrating the optical path adjustment state thereof.
Figure 4B:
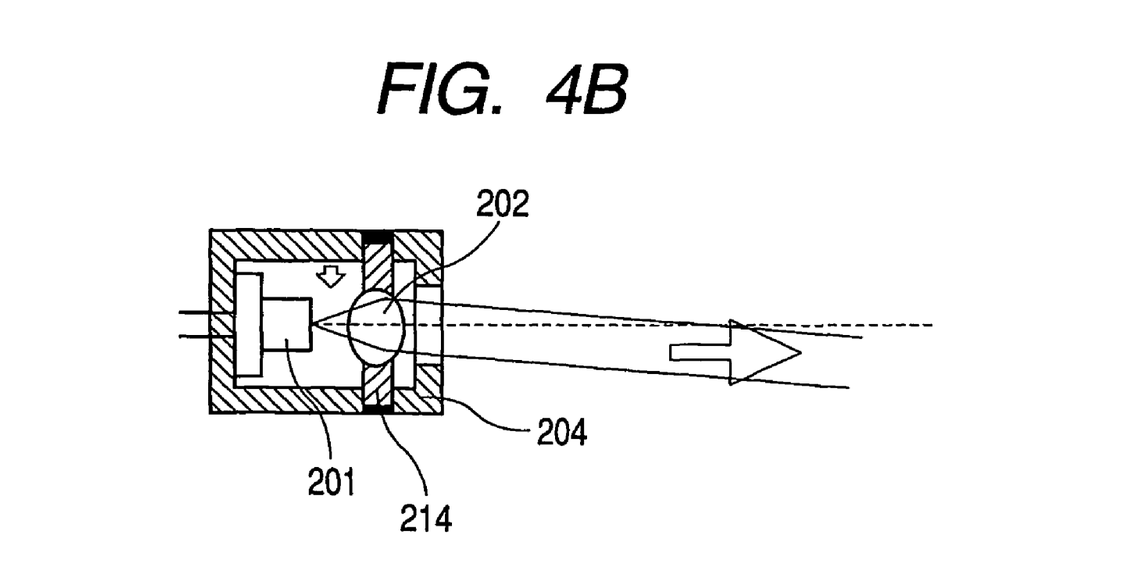

FIGS. 4A and 4B show a modification of the optical path-adjusting assemblies. In this modification, light-emission unit 104 has a movable cell 214 for shifting the position of collimator lens 202 (for parallelizing roughly the light emitted from semiconductor laser 201) vertically relative to the light traveling direction. Movable cell 214 moves collimator lens 202 to change the light emission angle of the parallel light.

The construction of detection unit 105 of this embodiment shown in FIG. 1 is explained below in detail by reference to FIGS. 5A and 5B.

Figure 5A:
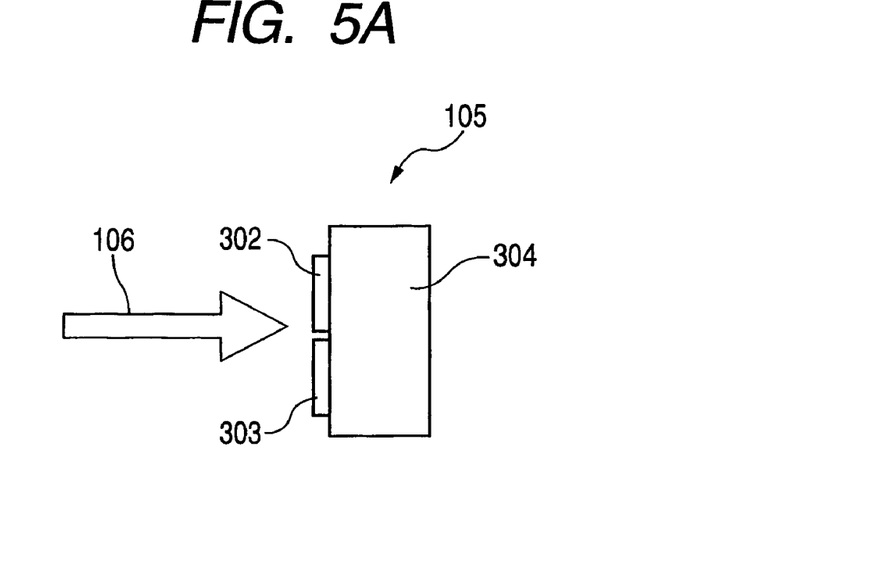
FIGS. 5A and 5B are respectively a front view of the detection unit of the detection device of FIG. 1; and a block diagram illustrating the circuit constitution thereof.
Figure 5B:
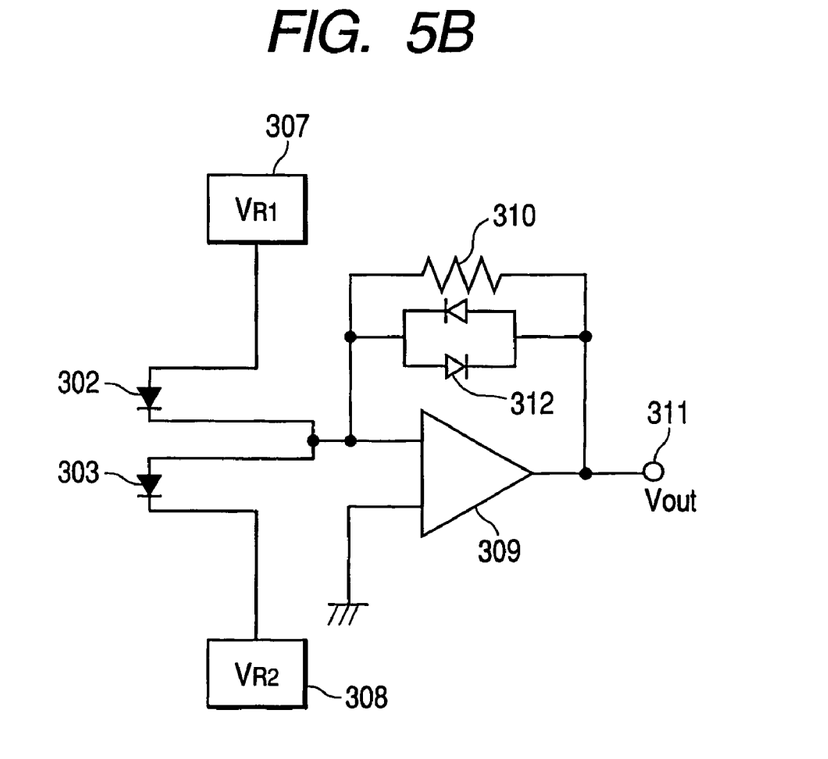

As shown in FIG. 5A, first photodiode (PD) 302 and second photodiode (PD) 303 are placed side by side on a plane to receive detecting light 106. In treatment assembly 304 holding the both PDs connected thereto, an electric circuit is formed for differential detection having basic constitution as shown in FIG. 5B. First PD 302 and second PD 303 are connected in the same direction in series, and the other ends of the connected PDs are respectively connected to reverse bias voltage sources 307, 308. The reverse bias voltages are adjustable depending on the light quantity introduced to first PD 302 and second PD 303, the amplification circuit in the later step, and so forth. The joint of first PD 302 and second PD 303 is connected to an amplification circuit comprising op-amp (operational amplifier) 309 and feedback resistance 310 to amplify the output voltage. The amplified output voltage $V_{out}$ is taken out from output terminal 311 and is detected.

Diode circuit 312 for a limiter having two diodes serves to limit the differential output from first PD 302 and second PD 303 when the differential output is excessively large, whereby the detection is made sensitive around the range where the two output voltages are balanced. Diode circuit 312 as the limiter is provided to conduct sensitive detection even when deflection of the detecting light 106 is small. This diode circuit 312 may be omitted in the case where the measurement is conducted mainly for large deflection of detecting light 106.

Being not shown in the drawing, first PD 302 and second PD 303 may be respectively provided with an independent amplification circuit and an independent voltage detector for allotting the output voltages to constitute an analog or digital circuit for calculating the sum S and the difference D of the two output voltages. With this constitution, a normalized differential output Sn=S/D can be derived and outputted. Thereby, even if the light quantity of detecting light 106 passing through reference flow channel 102 is decreased owing to absorption or scattering, the influence of drop of the light quantity can be canceled based on the sum S of the output voltages detected by two PDs 302, 303 to enable precise detection of the deflection of the light path.

SECOND EMBODIMENT

Figure 6:
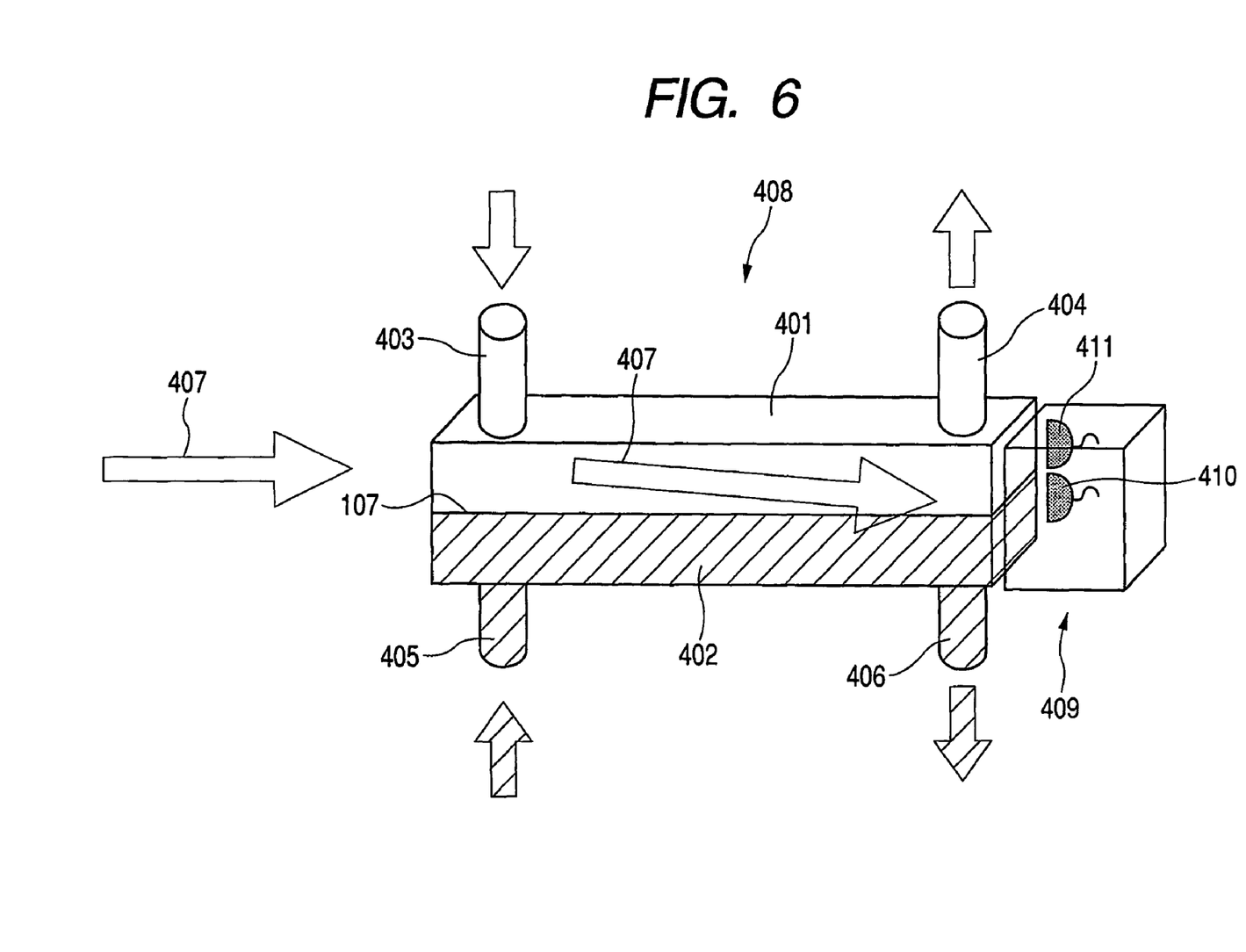
FIG. 6 is a schematic perspective view of constitution of the detection device of Second Embodiment of the present invention.
Figure 7:
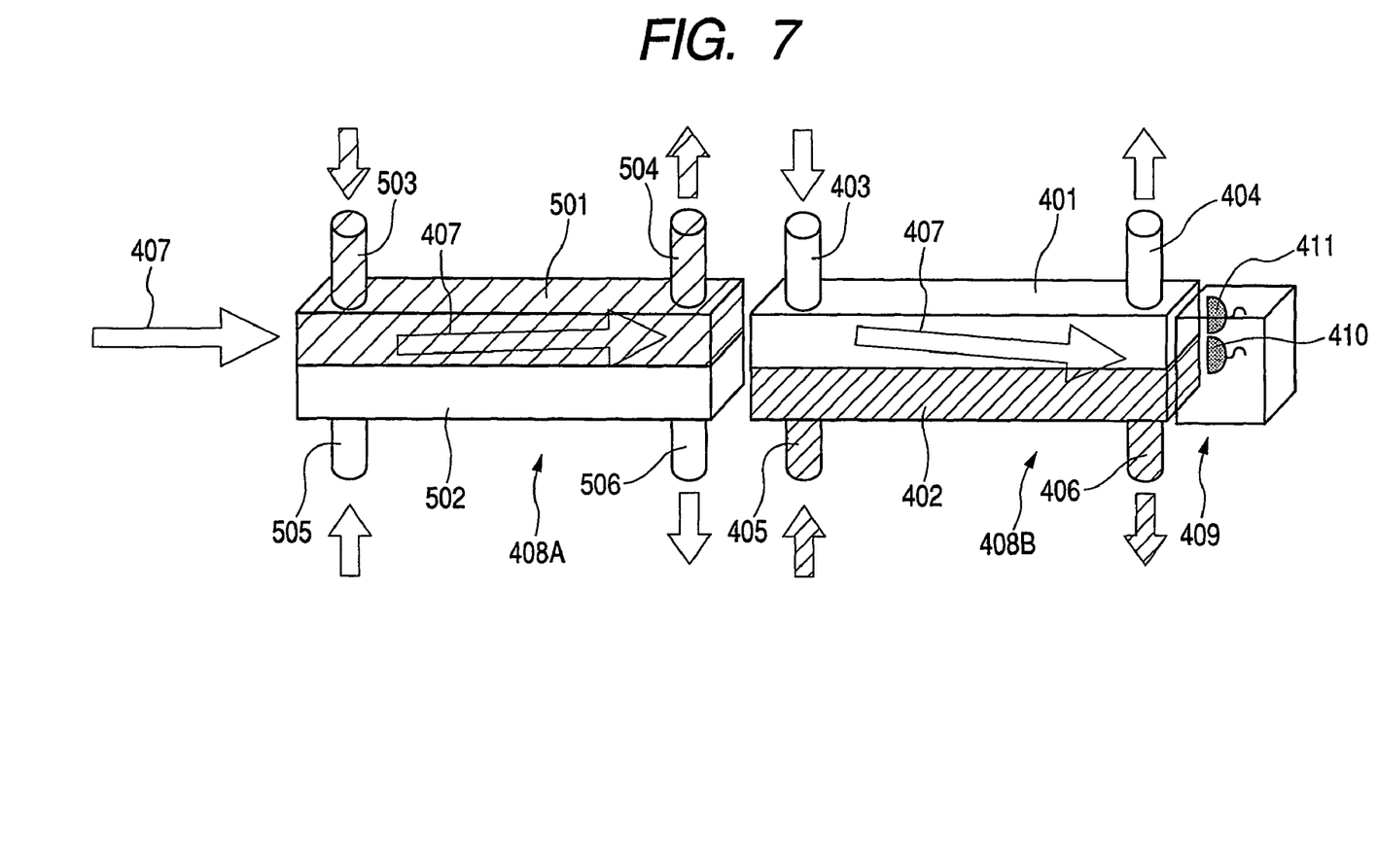
FIG. 7 is a schematic perspective view of a modification of the detection device of FIG. 6.

A second embodiment is explained below by reference to FIGS. 6 and 7. In FIGS. 6 and 7, the same members as in First Embodiment are denoted by the same symbols without explanation.

The detection device of this Embodiment, as shown in FIG. 6, similarly as First Embodiment, is provided with reference flow channel 401 and examination flow channel 402 with interposition of semipermeable membrane 107; detection light 407 is allowed to pass through reference flow channel 401; and the transmitted detecting light is received by two photodiodes 411, 410 of a two-division sensor to detect the differential signal.

The detection device of this Embodiment is constituted characteristically of a light-emission unit (not shown in the drawing), flow channel portion 408, and detection unit 409 as separate modules respectively connected in series. To avoid interference between the introduction and the discharge of the fluid to or from flow channels 401, 402 in the serial connection, introduction paths 463, 405 and discharge paths 404, 406 are provided in direction vertical to flow channel 401, 402 respectively.

In such a serial constitution, plural flow channel modules can be arrange in series between the light-emission module and the detection module. For example, as shown in FIG. 7 schematically, two flow-modules 408A, 408B having reference flow channels and examination channels separated independently are arranged in series with fluid inlets (503 and 403; 505 and 405) and fluid outlets (504 and 404; 506 and 406) being not shared such that reference flow channels 501, 401 are arranged serially and examination flow channels 502, 402 are arranged serially. With this arrangement, the optical path of detecting light 407 passes successively through the flow channels. Thereby, detection module 409 detects the sum of the deflections caused by two flow modules 408A, 408B, enabling total measurement at a time.

When total measurement is conducted by arranging many flow channels in series and providing a light-emission unit and a detection unit for each of the flow channel pairs without employing the independent module constitution of this Embodiment, electrical calculation circuits as well as the plural light-emission units and plural detection units are necessary for each of the flow channel pairs. These units and circuits are relatively expensive, and make the constitution complicated to prevent miniaturization and high integration of μ-TAS, biological chips, and the like, disadvantageously. The constitution of this Embodiment enables arrangement of three or more flow modules between a light-emission module (not shown in the drawing) and detection module 409. Thereby the above disadvantage is canceled.

Further, in the constitution shown in FIG. 7, in the adjacent two flow channel modules 408A, 408B, the arrangement of the high-concentration flow channels (e.g., examination flow channel) and the low-concentration flow channels (e.g., reference flow channel) may be reversed to each other. With this arrangement, in the second flow channel module 408B, detecting light 407 is deflected in the direction reverse to the deflection direction in the first flow channel module 408A. Thereby, calculation can be conducted with a plus or minus sign with the serial arrangement. In an application of such a constitution, the flow channels are arranged to obtain a plus-minus calculation result of zero: a plurality of the same flow channel pairs are arranged in series with reversal of the adjacent channel pairs. Thereby, the calculation result is zero in average, and the detecting light beam fluctuates in accordance with fluctuation of the concentration distribution. The detected fluctuation of the detecting light gives not only the average of the concentration distribution (low-level information) but also high-level information such as concentration fluctuation.

THIRD EMBODIMENT

A third embodiment of the present invention is explained below by reference to FIGS. 8 and 9A to 9D. In FIGS. 8 and 9A to 9D, the same members as in First and Second Embodiments are denoted by the same symbols without explanation.

Figure 8:
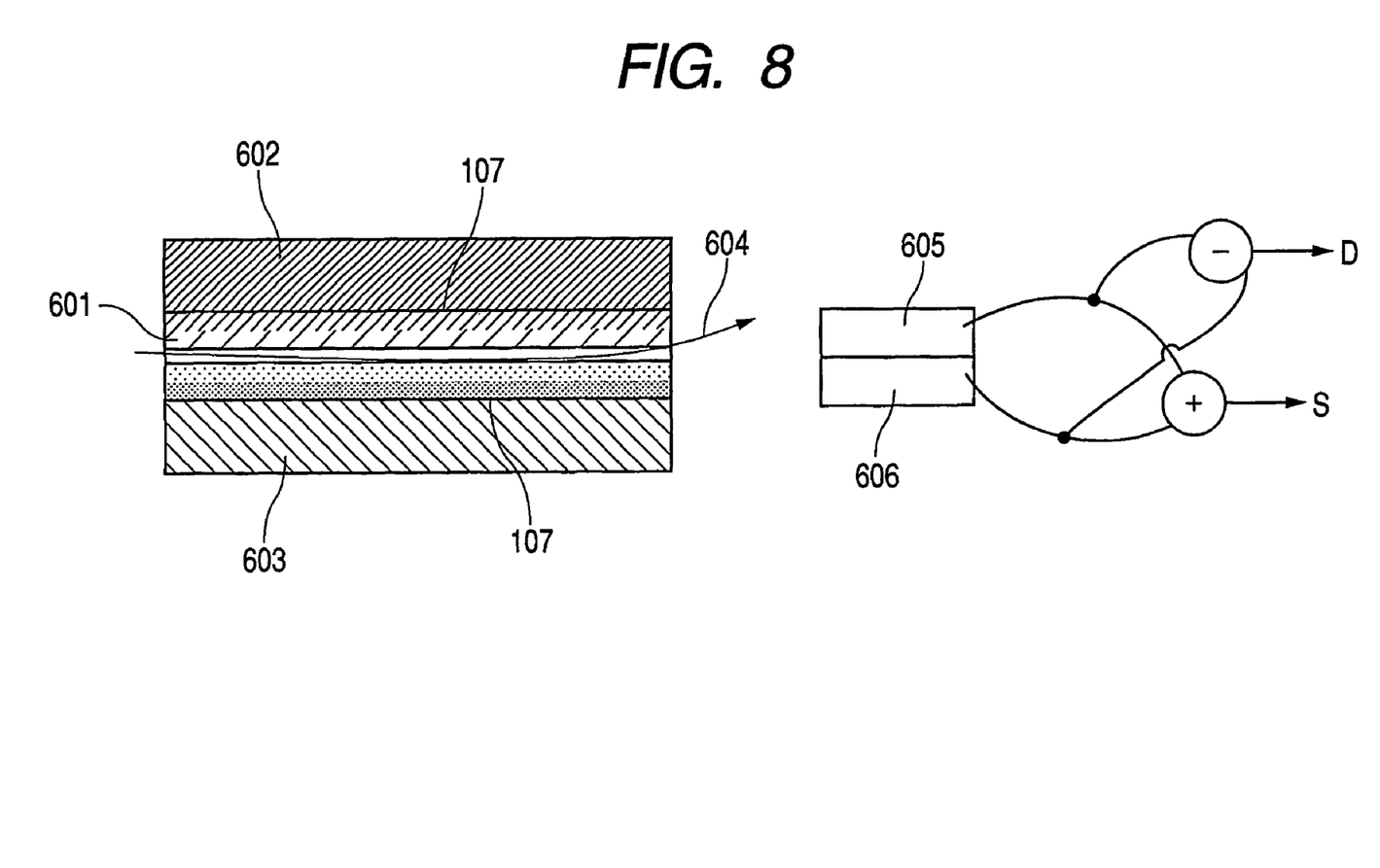
FIG. 8 is a schematic perspective view of constitution of the detection device of Third Embodiment of the present invention.

The detection device of this Embodiment comprises one reference flow channel 601, and two examination flow channels 602, 603 placed on the both sides of the reference channel with interposition of semipermeable membrane 107 respectively. Detecting light 604 is allowed to pass through reference flow channel 601, and the differential signal is detected by receiving detecting light 604 by two photodiodes 605, 606 of a two-division sensor.

In this Embodiment, different examination-objective fluids are allowed to flow through upper examination flow path 602 and lower examination flow path 603 on the both sides of reference flow channel 601. Thereby, the concentration distributions of the detection-objective substances in reference flow channel 601 become nonuniform, resulting in nonuniform distribution of the refractive index. Detecting light 604 passing through the nonuniform reference flow channel 601 is deflected in accordance with the nonuniform refractive index distribution, and is introduced into two photodiodes 605, 606 to be detected as a normalized differential output. Incidentally, the nonuniform state in this Embodiment signifies a state of an unsymmetrical distribution of the concentrations with respect to the center line of the reference flow channel and perpendicular to the arrangement direction of the reference flow channel and the examination flow channels in the cross-section of the flow channels.

Figure 9A:
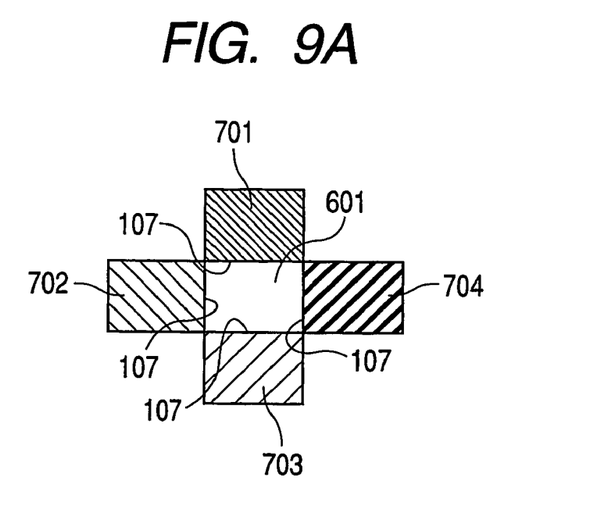
FIGS. 9A, 9B, 9C, and 9D are respectively a schematic side view of the flow channel of a modification of the detection device of FIG. 8; a schematic side view of the light-receiving part thereof; a schematic side view of the flow channel portion of another modification; and a schematic side view of the light-receiving portion thereof.
Figure 9B:
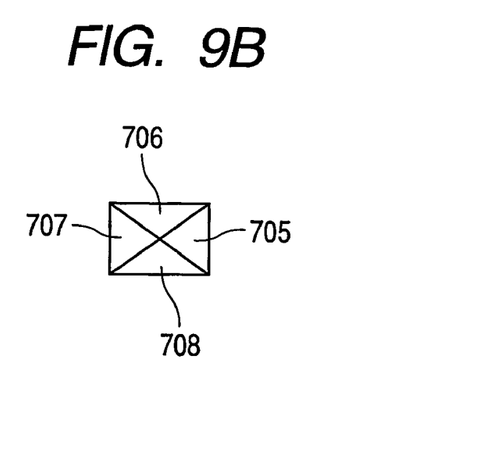
Figure 9C:
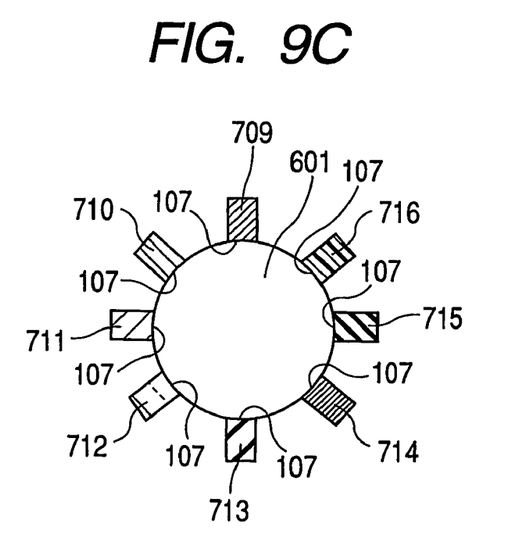
Figure 9D:
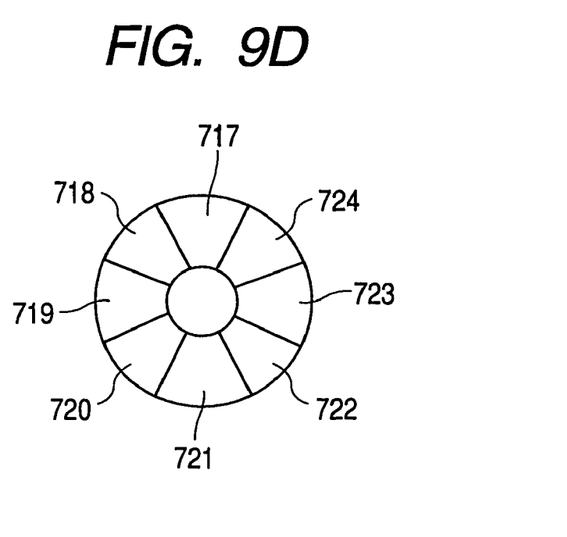

This Embodiment includes modifications which has plural examination flow channels adjacent to reference flow channel 601 as shown in FIGS. 9A to 9C.

In the constitution shown in FIG. 9A, four examination flow channels 701 to 704 are provided around reference flow channel 601 with interposition of a semipermeable membrane 107. The deflection of the detecting light is measured two-dimensionally by four photodiodes 705 to 708 of a four-division sensor. The four output signals from the four photodiodes are suitably divided or combined to derive a difference signal, and a sum signal for normalization by calculation circuit not shown in the drawing. From the calculation results, the quantities of the substances having penetrated through semipermeable membrane 107, and the concentrations of the substances in examination flow channels 701 to 704 are measured.

In the constitution shown in FIG. 9C, eight examination flow channels 709 to 716, larger in number than above, are provided around cylindrical reference flow channel 601 with interposition of semipermeable membrane 107 respectively. The state of deflection of the detecting light is determined precisely by eight photodiodes 717 to 724 constituting an eight-division sensor shown in FIG. 9D. The eight output signals from the eight photodiodes are suitably divided or combined to derive a difference signal, and a sum signal for normalization by a calculation circuit (not shown in the drawing). From the calculation results, the quantities of the substances having penetrated through semipermeable membrane 107, and the concentrations of the substances in examination flow channels 709 to 716 are determined.

FOURTH EMBODIMENT

Figure 10:
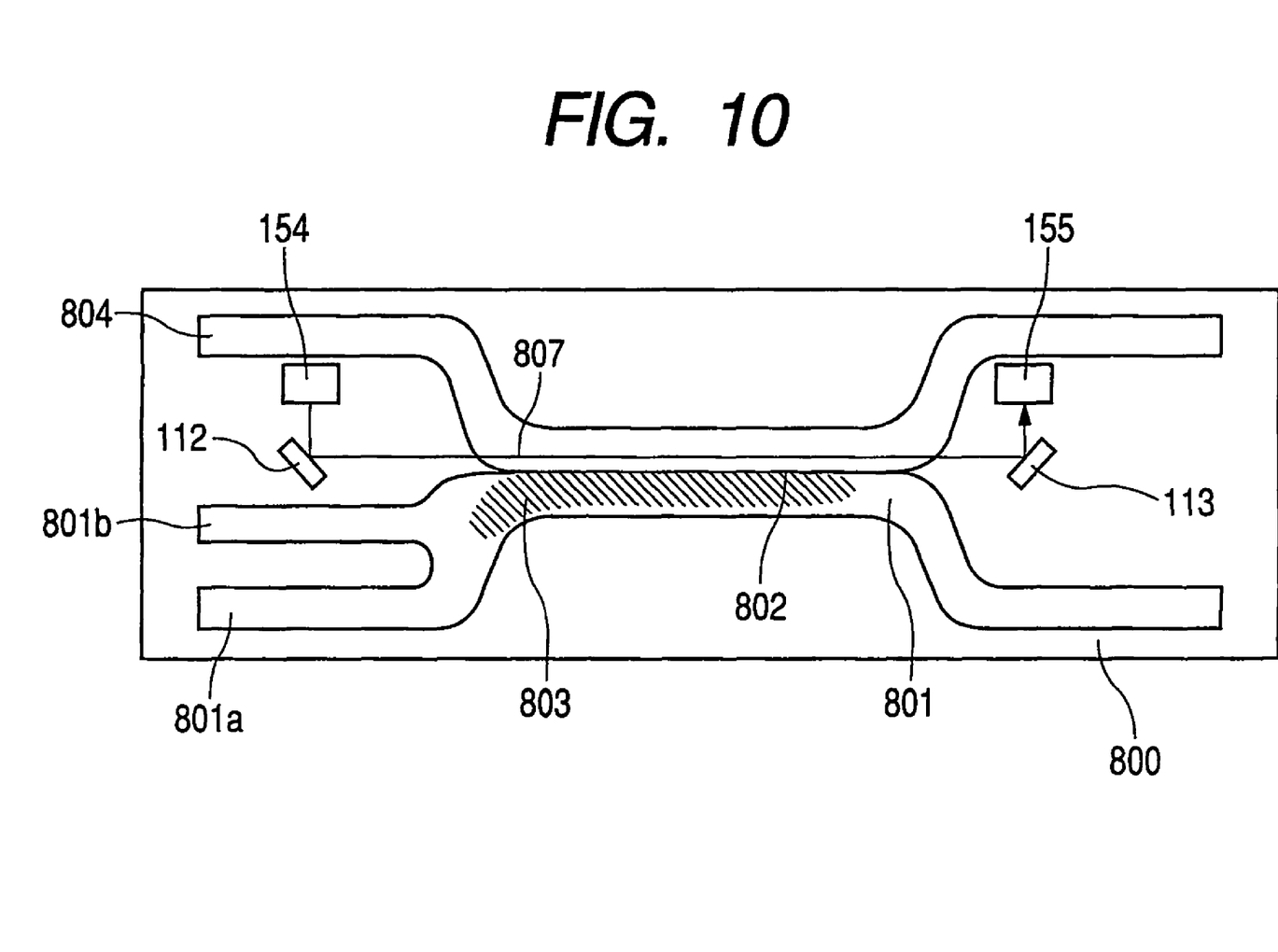
FIG. 10 is a perspective view of constitution of the detection device of Fourth Embodiment of the present invention.

A fourth embodiment of the present invention is explained below by reference to FIG. 10. In FIG. 10, the same members as in First to Third Embodiments are denoted by the same symbols without explanation.

The detection device of this Embodiment comprises a plate-shaped functional module 800 of a μ-TAS as shown in FIG. 10. This functional module 800 is used for detecting reaction heat of a chemical reaction. This module has reference flow channel 804 and reaction flow channel (examination flow channel) 801 having branched fluid inlets 801a, 801b. The boundary between reference flow channel 804 and examination flow channel 801 is constructed from a heat-conductive film 802, not from a semipermeable membrane. The base material of heat-conductive film 802 includes metals such as copper, gold, silver, and aluminum. This heat-conductive film 802 transmits heat from examination flow channel 801 to reference flow channel 804 depending on the temperature difference.

Solutions which will react on mixing are respectively introduced from fluid inlets 801a, 801b. A reference fluid is introduced into the reference flow channel 804.

The solutions introduced into fluid inlets 801a, 801b react chemically at the joint portion in examination flow channel 801. The reaction generates reaction heat to cause temperature rise. The reaction heat is transmitted through heat-conductive film 802 to reference flow channel 804, raising the temperature of the reference fluid. The temperature rise of the reference fluid is largest at the portion near reaction region 803, decreasing with the distance from the reaction region 803. Thereby the temperature distribution is nonuniform in reference flow channel 804. This temperature distribution causes refractive index distribution according to the temperature coefficient of the refractive index dn/dT. Thus detecting light 807 emitted from light emission unit main body 154 and introduced through optical path-adjusting assembly 112 into reference flow channel 804 is deflected according to the refractive index distribution, and is introduced through optical path-adjusting assembly 113 into detection unit main body 155. The light reception point in detection unit main body 155 shows the deflection of detecting light 807, and therefrom the temperature distribution in reference flow channel 804 is estimated, and further the reaction heat having transmitted through thermal conductive film 802 to examination flow channel 801 is derived.

The present invention is not limited to the above First to Fourth Embodiments, but includes various modifications of the sequences and other constitutions within the scope of the present invention.

This application claims priority from Japanese Patent Application No. 2003-408933 filed Dec. 8, 2003, which is hereby incorporated by reference herein.

The invention claimed is:

1. A detection device for detecting a concentration of a detection object, comprising:
    an examination flow channel for passing a first fluid containing a detection object, a reference flow channel for passing a second fluid, extending adjacently along the examination flow channel, a semi-permeable member located between the examination flow channel and the reference flow channel and capable of causing an interaction therebetween, a light emission unit for irradiating the second fluid in the reference flow channel, the light emission unit comprising a semiconductor laser and a turning micromirror to irradiate directly from the laser to a prescribed position, and a detection unit having a plurality of light receiving sensors for receiving the irradiated light by way of the reference flow channel, wherein the concentration of the detection object in the examination flow channel is recognized based on a deflection of an optical path of emitted light caused by a gradient index in the second fluid resulting from the interaction, and the deflection of the optical path is evaluated by differential output of the plurality of light receiving sensors.

2. The detection device according to claim 1, wherein the semi-permeable member is a heat-conductive film, and the interaction is heat transfer from the examination flow channel to the reference flow channel, and wherein the detection unit measures temperature change in the examination flow channel.

3. The detection device according to claim 2, wherein the examination flow channel has plural fluid inlets for introduction of different substances.

4. The detection device according to claim 2, wherein the detection unit comprises plural optical detectors arranged substantially in the direction of arrangement of the examination flow channel and the reference flow channel, and the deflection of the optical path of the detecting light is evaluated by differential output from the plural optical detectors.

5. The detection device according to claim 1, wherein the detection unit comprises plural optical detectors arranged substantially in the direction of arrangement of the examination flow channel and the reference flow channel, and the deflection of the optical path of the detecting light is evaluated by differential output from the plural optical detectors.

6. A detection method for detecting a concentration of a detection object comprising the steps of:

providing a detection device having an examination flow channel, a reference flow channel extending adjacently along the examination flow channel, and a semi-permeable member located between the examination flow channel and the reference flow channel for causing an interaction therebetween, introducing a first fluid containing a detection object into the examination flow channel and a second fluid into the reference flow channel, irradiating the second fluid in the reference flow channel using a semiconductor laser and a turning micromirror to irradiate directly from the laser to a prescribed position, and measuring a deflection of an optical path of emitted light caused by a gradient index in the second fluid resulting from the interaction with a detecting unit having a plurality of light receiving sensors to detect the concentration of the detection object, wherein the deflection of the optical path is evaluated by differential output of the plurality of light receiving sensors.

7. The detection device according to claim 1, wherein the turning micromirror is rotatable to adjust the optical path of the emitted light.

8. The detection device according to claim 1, wherein the turning micromirror includes an adjusting unit to turn the micromirror and adjust the optical path of the emitted light.

9. The detection device according to claim 1, wherein the detection unit further comprises an optical path adjusting assembly to adjust the optical path of the emitted light.

10. The detection method according to claim 6, further comprising the step of rotating the turning micromirror to adjust the optical path of the emitted light.

11. The detection method according to claim 6, further comprising the step of providing the detection unit with an optical path adjusting assembly and adjusting the optical path of the emitted light.

* * * * *